United States Patent
Lai

(10) Patent No.: US 8,790,104 B2
(45) Date of Patent: Jul. 29, 2014

(54) APPARATUS AND METHOD OF FABRICATING A COMPENSATING ELEMENT FOR WAVEFRONT CORRECTION USING SPATIALLY LOCALIZED CURING OF RESIN MIXTURES

(75) Inventor: Shui T. Lai, Encinitas, CA (US)

(73) Assignee: Essilor International (Compagnie Generale d'Optique, Charenton Cedex (FR)

( * ) Notice: Subject to any disclaimer, the term of this patent is extended or adjusted under 35 U.S.C. 154(b) by 769 days.

(21) Appl. No.: 12/437,506

(22) Filed: May 7, 2009

(65) Prior Publication Data

US 2009/0212465 A1 Aug. 27, 2009

Related U.S. Application Data

(60) Division of application No. 11/749,058, filed on May 15, 2007, now abandoned, which is a continuation of application No. 10/265,517, filed on Oct. 3, 2002, now Pat. No. 7,217,375.

(51) Int. Cl.
*B29D 11/00* (2006.01)
(52) U.S. Cl.
USPC .......... 425/174.4; 264/1.1; 264/1.7; 351/205; 425/808
(58) Field of Classification Search
USPC ............... 425/174.4, 808, 810; 264/1.1, 1.37, 264/494, 496, 1.36, 1.7; 351/205
See application file for complete search history.

(56) References Cited

U.S. PATENT DOCUMENTS

| | | |
|---|---|---|
| 3,933,411 A | 1/1976 | Winner |
| 3,973,837 A | 8/1976 | Page |
| 4,022,855 A | 5/1977 | Hamblen |
| 4,268,133 A | 5/1981 | Fischer et al. |
| 4,666,236 A | 5/1987 | Mikami et al. |
| 4,810,070 A | 3/1989 | Suda et al. |
| 4,848,894 A | 7/1989 | Buser et al. |
| 4,869,587 A | 9/1989 | Breger |

(Continued)

FOREIGN PATENT DOCUMENTS

| | | |
|---|---|---|
| EP | 0 472 384 | 8/1991 |
| EP | 0 485 197 | 5/1992 |

(Continued)

OTHER PUBLICATIONS

International Search Report for Application No. PCT/US03/24150, dated on Nov. 26, 2003, filed on Jul. 30, 2003.

(Continued)

*Primary Examiner* — Mathieu D. Vargot
(74) *Attorney, Agent, or Firm* — Cozen O'Connor

(57) ABSTRACT

An optical wavefront correction plate incorporates a unique, three-dimensional spatial retardation distribution utilizing the index of refraction change of resin mixture in its cured state. The optical wave plate comprises a pair of transparent plates, containing a layer of a monomers and polymerization initiators, such as resin mixture. This resin mixture exhibits a variable index of refraction as a function of the extent of its curing. Curing of the resin mixture may be made by exposure to light, such as ultraviolet light, and may be varied across and through the surface of the resin mixture to create a particular and unique three-dimensional wavefront retardation profile. The optical wave plate provides improved performance in large area mirrors, lenses, telescopes, microscopes, and ophthalmic diagnostic systems.

18 Claims, 10 Drawing Sheets

(56) References Cited

U.S. PATENT DOCUMENTS

| | | | |
|---|---|---|---|
| 4,874,234 A | 10/1989 | Wichterle | |
| 4,969,729 A | 11/1990 | Merle | |
| 4,996,123 A | 2/1991 | Nomura et al. | |
| 5,054,888 A | 10/1991 | Jacobs et al. | |
| 5,080,472 A | 1/1992 | Gupta | |
| 5,100,589 A | 3/1992 | Ticknor | |
| 5,114,628 A | 5/1992 | Hofer et al. | |
| 5,116,684 A | 5/1992 | Fretz, Jr. et al. | |
| 5,148,205 A | 9/1992 | Guilino et al. | |
| 5,198,844 A | 3/1993 | Roffman et al. | |
| 5,200,858 A | 4/1993 | Hagerty et al. | |
| 5,223,862 A | 6/1993 | Dasher et al. | |
| 5,229,797 A | 7/1993 | Futhey et al. | |
| 5,266,352 A | 11/1993 | Filas et al. | |
| 5,343,260 A | 8/1994 | Henry et al. | |
| 5,372,755 A | 12/1994 | Stoerr et al. | |
| 5,433,810 A | 7/1995 | Abrams | |
| 5,448,312 A | 9/1995 | Roffman et al. | |
| 5,528,321 A | 6/1996 | Blum et al. | |
| 5,585,968 A | 12/1996 | Guhman et al. | |
| 5,606,378 A | 2/1997 | Van Meurs | |
| 5,608,471 A | 3/1997 | Miller | |
| 5,617,154 A | 4/1997 | Hoffman | |
| 5,650,837 A | 7/1997 | Roffman et al. | |
| 5,715,031 A | 2/1998 | Roffman et al. | |
| 5,771,088 A | 6/1998 | Perrott | |
| 5,777,719 A | 7/1998 | Williams et al. | |
| 5,786,883 A | 7/1998 | Miller et al. | |
| 5,835,192 A | 11/1998 | Roffman et al. | |
| 5,861,934 A | 1/1999 | Blum et al. | |
| 5,864,379 A | 1/1999 | Dunn | |
| 5,872,613 A | 2/1999 | Blum et al. | |
| 5,880,809 A | 3/1999 | Lieberman et al. | |
| 5,907,386 A | 5/1999 | Gupta et al. | |
| 5,929,969 A | 7/1999 | Roffman | |
| 5,949,521 A | 9/1999 | Williams et al. | |
| 5,953,098 A | 9/1999 | Lieberman et al. | |
| 5,956,183 A | 9/1999 | Epstein et al. | |
| 5,981,616 A * | 11/1999 | Yamamura et al. | 522/168 |
| 5,998,096 A | 12/1999 | Umemoto et al. | |
| 6,027,672 A | 2/2000 | Weitzel et al. | |
| 6,081,632 A | 6/2000 | Yoshimura et al. | |
| 6,086,204 A | 7/2000 | Magnante | |
| 6,089,711 A | 7/2000 | Blankenbecler et al. | |
| 6,109,749 A | 8/2000 | Bernstein | |
| 6,139,147 A | 10/2000 | Zhang | |
| 6,176,580 B1 | 1/2001 | Roffman et al. | |
| 6,240,226 B1 | 5/2001 | Presby et al. | |
| 6,274,288 B1 | 8/2001 | Kewitsch et al. | |
| 6,319,433 B1 | 11/2001 | Kohan | |
| 6,328,446 B1 | 12/2001 | Bhalakia et al. | |
| 6,379,005 B1 | 4/2002 | Williams et al. | |
| 6,390,623 B1 | 5/2002 | Kokonaski et al. | |
| 6,450,642 B1 | 9/2002 | Jethmalani et al. | |
| 6,499,843 B1 | 12/2002 | Cox et al. | |
| 6,554,425 B1 | 4/2003 | Roffman et al. | |
| 6,712,466 B2 * | 3/2004 | Dreher | 351/159.01 |
| 6,786,602 B2 | 9/2004 | Abitbol | |
| 2002/0080464 A1 * | 6/2002 | Bruns | 359/290 |
| 2002/0196412 A1 | 12/2002 | Abitbol | |
| 2003/0081172 A1 | 5/2003 | Dreher | |

FOREIGN PATENT DOCUMENTS

| | | |
|---|---|---|
| EP | 0 887 687 | 12/1998 |
| EP | 0 949 529 | 4/1999 |
| EP | 0 942 312 | 9/1999 |
| GB | 1045065 | 10/1966 |
| JP | 57-053702 | 3/1982 |
| JP | 59-114030 | 6/1984 |
| JP | 60-175009 | 9/1985 |
| JP | 06-297595 | 10/1994 |
| JP | 10-006403 | 1/1998 |
| JP | 11-242192 | 9/1999 |
| JP | 2000-199876 | 7/2000 |
| JP | 2001-166106 | 6/2001 |
| WO | WO-86/01308 | 2/1986 |
| WO | WO-89/01640 | 2/1989 |
| WO | WO-94/14567 | 7/1994 |
| WO | WO-98/53360 | 11/1998 |
| WO | WO-99/13361 | 3/1999 |
| WO | WO-99/34239 | 7/1999 |
| WO | WO-99/34248 | 7/1999 |
| WO | WO-00/41650 | 7/2000 |
| WO | WO-01/02896 | 1/2001 |
| WO | WO-01/89424 | 11/2001 |
| WO | WO-01/96917 | 12/2001 |
| WO | WO-02/13728 | 2/2002 |
| WO | WO-02/26121 | 4/2002 |
| WO | WO-02/32297 | 4/2002 |
| WO | WO-03/058296 | 7/2003 |

OTHER PUBLICATIONS

Moretti, "New laser-based technologies incubate," Opthamology News, Nov. 29, 2001.
European Office Action for Application No. 03 808 084.2, dated Jun. 27, 2008, 3 pages.
European Search Report for EP 06020933.5, mailed Jun. 18, 2008, 5 pages.
Notice of Reasons for Rejection for Japanese Patent Application No. 2004-527710, mailed on Sep. 16, 2008, 8 pages.
Non-Final Office Action for U.S. Appl. No. 11/869,607, mailed on Apr. 23, 2009, 14 pages.

* cited by examiner

APPARATUS AND METHOD OF FABRICATING A COMPENSATING ELEMENT FOR WAVEFRONT CORRECTION USING SPATIALLY LOCALIZED CURING OF RESIN MIXTURES

RELATED APPLICATIONS

This application is a divisional of U.S. patent application Ser. No. 11/749,058, filed May 15, 2007, now abandoned which is continuation of U.S. patent application Ser. No. 10/265,517, filed Oct. 3, 2002, now U.S. Pat. No. 7,217,375.

BACKGROUND OF THE INVENTION

1. Field of the Invention

The present invention relates generally to producing optical elements for use in optical systems.

2. Description of the Related Art

In many optical systems it is common to assume that the light passing through the system is limited to paraxial rays, specifically, rays that are near the optical axis and that are sustained within small angles. With this assumption, corrective optics having only spherical surfaces can correct aberrations that are present in images generated by the optical systems. While aspheric optics can be produced, to do so is costly and time consuming.

An example of the above problem is the human eye. It is conventionally assumed that ocular imperfections are limited to lower order imperfections, including the imperfections commonly called "astigmatism" and "defocus", that can be corrected by lenses having spherical surfaces. However, in reality optical systems including the human eye rarely are limited to what is conventionally assumed for purposes of providing corrective optics that have only spherical surfaces. In the case of the human eye, for instance, higher order imperfections can exist, including but not limited to those imperfections known as "coma" and "trefoil". These imperfections unfortunately cannot be corrected by conventional glasses or contact lenses, leaving patients with less than optimum vision even after the best available corrective lenses have been prescribed.

Moreover, as recognized by the present invention, it is often difficult to simultaneously minimize all aberrations. Indeed, corrections to an optical system to minimize one type of aberration may result in the increase in one of the other aberrations. As but one example, decreasing coma can result in increasing spherical aberrations.

Furthermore, it is often necessary to correct aberrations in an optical system that are introduced during manufacturing. This process can be iterative and time consuming, requiring, as it does, assembly, alignment, and performance evaluation to identify aberrations, followed by disassembly, polishing or grinding to correct the aberrations, and then reassembling and retest. Several iterations might be needed before a suitable system is developed.

Having recognized the above-noted problems, the invention provides the below-disclosed solutions to one or more of them.

SUMMARY OF THE INVENTION

The present invention is related to optical elements having a variable and predetermined, three-dimensional spatial retardation distribution and related systems and methods for making such optical elements.

The optical element of one embodiment of the present invention includes a cavity. The cavity can be formed by a pair of transparent windows, or plates with a retaining ring, or spacer between the plates. The cavity is filled with one or more monomers, or pre-polymers, monomer mixtures and polymerization initiators (referred to generally herein as a resin mixture). This resin mixture exhibits an index of refraction change as it polymerizes, and the change is controlled by the extent of its polymerization, or curing. The curing of the resin mixture may be initiated by exposure to light, such as ultraviolet light. The exposure to light may be controlled spatially across and through the resin mixture to create a predetermined three-dimensional wavefront retardation profile. One application of such a wavefront retardation plate is to cancel the aberrations in an optical system, such that when an ideal plane wave passes through the wavefront retardation plate, a predetermined change of the wavefront profile can be affected by the wave plate, and when the wavefront subsequently passes through the optical system, aberrations introduced by the system (except for the intended focusing of the system) are cancelled. Alternatively, if the goal of the optical system is to establish a cylindrical lens, all aberration terms are cancelled, except for the desired astigmatism terms. Embodiments of the present invention have the ability to produce any retardation, including any one or any combination of the aberrations as describable by the Zernike polynomials.

The present invention is also applicable to the manufacturing of all conventional and specialized optical elements, including aspheric and other refractive surfaces, refractive elements (e.g., lenses), reflective elements (e.g., mirrors and beam splitters), and/or diffractive elements such as gratings, and Fresnel optics.

DETAILED DESCRIPTION

Figure 1:
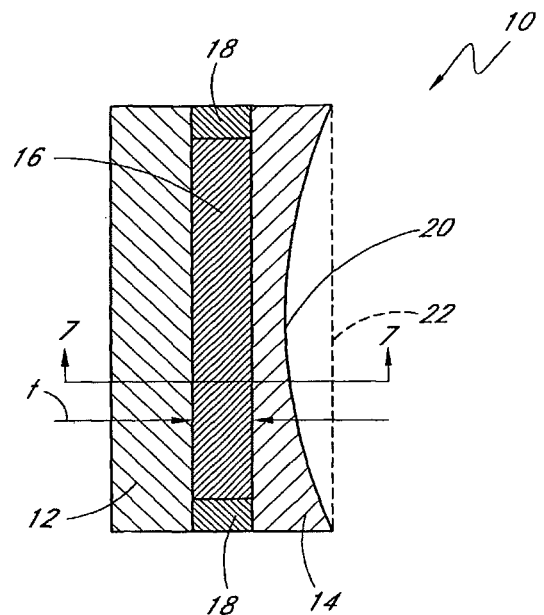
FIG. 1 is a cross-sectional view of a correcting element.

Referring initially to FIG. 1, a correcting element of the present invention is shown, generally designated 10. As shown, the correcting element 10 includes a first rigid or flexible transparent plate 12, a second rigid or flexible transparent plate 14, and a layer of resin mixture 16 sandwiched therebetween. If desired, a barrier 18 can be used to contain the resin mixture 16 between the plates 12, 14 prior to, and following, the below-described curing of the resin mixture.

The term "resin mixture," as used herein, is intended to include light-curable resins comprised of one or more monomers, pre-polymers, polymers and polymerization initiators. The refractive index of the resin changes as the resin is cured, and it can be made to vary between locations within the resin layer depending on the spatial extent of curing of the resin mixture, as more fully disclosed below. The extent of curing is determined by the percentage of cross-linking between the monomers within the resin mixture. One non-limiting example of suitable resins is VLE-4101 UV-Visible Light CureEpoxy, available from Star Technology, Inc., or Optical Adhesive #63, U.V. Curing, available from Norland Products, Inc. Typically, these resins are curable by exposure to UV or visible light radiation in the range of 300 to 550 nanometers (300-550 nm). Generally, any type of material that exhibits an index of refraction change upon curing may be used and the corresponding curing light source may have appropriate curing wavelengths, e.g., wavelengths that are within the range of 250 nm to 3000 nm. Alternatively, the resin mixture can be cured by other radiation such as microwave or electron beam.

It is to be appreciated, however, that many suitable resins exist which exhibit a similar change in its index of refraction upon exposure to light. Other monomers that polymerize into long-chain molecules using photo-initiators may be used. For example, a suitable monomer may be chosen from the family of epoxides, urethanes, thiol-enes, acrylates, cellulose esters, or mercapto-esters, and a broad class of epoxies. Also, for example, a suitable photo-initiator may be chosen from alpha cleavage photoinitiators such as the benzoin ethers, benzil ketals, acetophenones, or phosphine oxides, or hydrogen abstraction photoinitiators such as the benzophenones, thioxanthones, camphorquinones, or bisimidazole, or cationic photoinitiators such as the aryldiazonium salts, arylsulfonium and aryliodonium salts, or ferrocenium salts. Alternatively, other photoinitiators such as the phenylphosphonium benzophene salts, aryl tert-butyl peresters, titanocene, or NMM may be used.

As shown in FIG. 1, the second transparent plate 14 includes an outwardly-facing curved surface 20 which may exhibit a pre-existing refractive power. Alternatively, transparent plate 14 may be planar, as represented by the dashed line 22.

It is to be understood that the resin mixture 16 may be formed with a predetermined thickness "t" such that a predetermined volume is established between the plates 12, 14, and barrier 18. As understood herein, the thickness and/or volume of resin mixture 16 can be established as appropriate to provide a correcting element having any desirable spatial retardation distribution utilizing the index of refraction change of resin mixture in its cured state.

Figure 2:
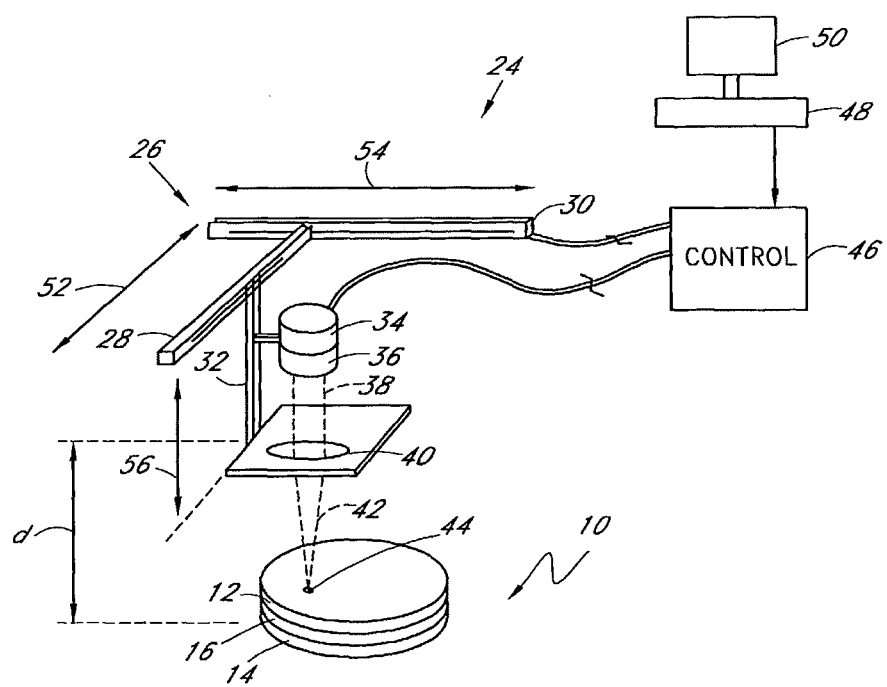
FIG. 2 is a schematic diagram of a first preferred apparatus for establishing a correcting element.

Referring now to FIG. 2, a system generally designated as 24, is shown for curing the resin mixture 16 of the correcting element 10. As shown, the system 24 includes an X-Y-Z scanning unit 26 having an X-direction rail 28 and an Y-direction rail 30. Also, the system 24 includes a Z-direction rail 32 extending from the X- or Y-direction rails. Moreover, a light source 34 having a beam shaping unit 36 is attached to and is movable on the Z-direction rail 32. The beam shaping unit 36 may include spatial filtering and beam collimation components to produce a higher quality beam.

FIG. 2 shows that the light source 34, in combination with the beam shaping unit 36, create a light beam 38 which, in a preferred embodiment, is substantially collimated. It should be appreciated, however, that a non-collimated beam may also be used if desired. In one exemplary, non-limiting embodiment, the light beam 38 passes through a focusing lens 40 to form a converging, or focusing, light beam 42 that is directed toward the correcting element 10, where the light beam 42 passes through the first transparent plate 12 to focus at 44 within the resin mixture layer 16, as shown and described further below in reference to FIG. 7. The focusing lens can be, e.g., a microscope objective piece with a large numerical aperture.

In any case, in accordance with present principles, the light source 34 irradiates the monomer (e.g., resin mixture 16), which activates the photo-initiator and begins the curing process within the resin mixture 16. The curing process results in a corresponding change of the index of refraction within the resin. Terminating the exposure to the light ceases the curing of the resin mixture, thereby ceasing the change of the index of refraction exhibited by the resin mixture. In this manner, the correcting element 10 is established by exposing predetermined portions of the resin mixture 16 to light.

As envisioned by the present invention, the activation and power level of the light source 34 and its position along the X-Y-Z axes may be controlled by a controller 46, which is electrically connected to the light source 34 and to shuttling components on the rails 28, and/or 30, and/or 32. The controller 46 can receive instructions regarding the desired index of refraction profile to be implemented from a computer 48 with associated monitor 50. More particularly, by moving the light source 34 along the rails 28, 30, 32 in the directions respectively indicated by arrows 52, 54, 56, and by establishing the power of the light source 34, curing volumes of differing sizes or the same sizes may be formed within the resin mixture 16. For instance, by delivering a lower intensity, or lower power level, from the light source 34, a spatially localized curing that is only immediately adjacent to the focal point 44 can be established, to create a relatively small curing volume. On the other hand, by delivering a higher intensity, or higher power level, from the light source 34, a spatially localized curing may include regions of resin mixture surrounding the focal point 44, to create a larger curing volume. Regardless, the depth in the resin mixture 16 of the focal point 44 is established by appropriately establishing the distance d between focusing lens 40 and resin mixture layer 16.

In a preferred embodiment, the power density of the light source 34 is controlled by controlling the current to the light source. Or, the amount of light delivered into the resin mixture 16 can be established using a constant light source 34 power level and variable light attenuator methods, including Pockel cells or other polarization rotation means and a polarized discriminator. It is to be understood that other light intensity control methods can also be used.

In a particularly preferred embodiment, the scanning unit 26 first forms the curing volumes which are farthest from the light source 34, i.e., which are deepest in the resin mixture 16. For instance, the scanning unit 26 would initially position the focal point of the light beam adjacent the bottom plate 14. The advantage of initially curing the resin mixture furthest from the light source is that the curing status of the entire resin mixture volume in the resin mixture layer 16 can be better controlled thereby. This method of photon energy delivery is particularly advantageous in those cases wherein the cured resin mixture becomes partially or substantially opaque at the curing wavelength post-curing, in which case the regions of the resin mixture 16 that would be behind the cured portion (i.e., furthest away from the light source 34) would otherwise become inaccessible for curing.

Figure 3:
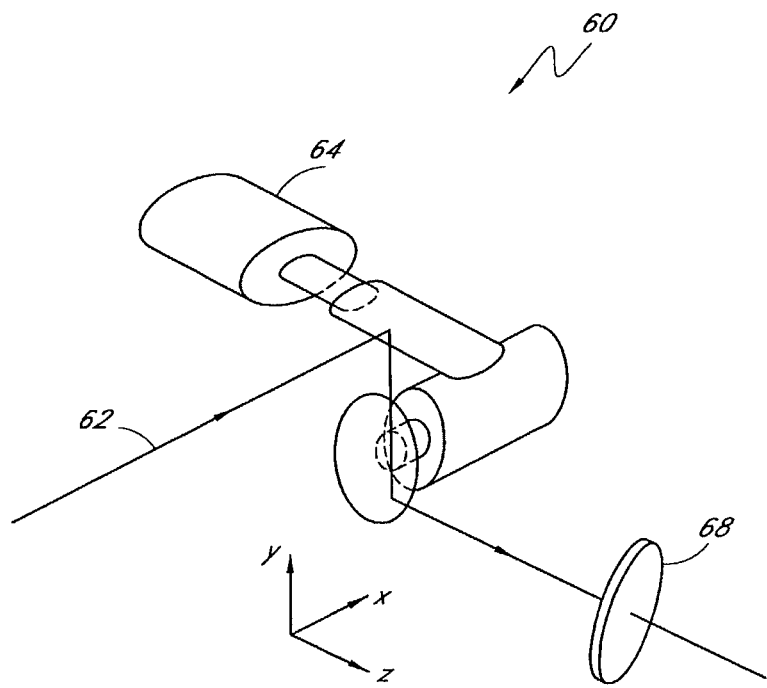
FIG. 3 is a schematic diagram of a second preferred apparatus for establishing a correcting element.
Figure 4:
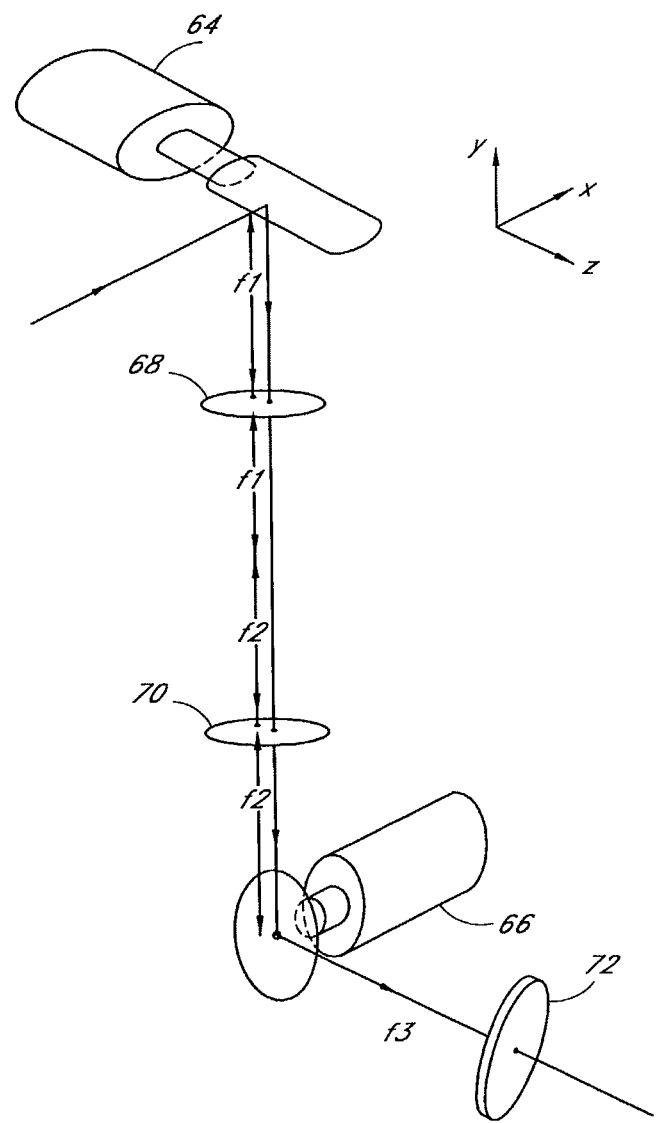
FIG. 4 is a schematic diagram of a third preferred apparatus for establishing a correcting element.

FIGS. 3 and 4 show related embodiments of another system, generally designated 60, that can be used to direct curing light onto the correcting element 10. A collimated light beam 62 is directed to a first beam scanner 64, which can be a single galvanometric type scanner for one dimensional scans as shown in FIG. 3. The light passes through a focussing lens 68 toward the target correcting element.

Or, two galvanometric scanners 64, 66 can be used as shown in FIG. 4, with their scan axes oriented orthogonal to each other, for generating two dimensional scan patterns in the X-Y plane. The scanners 64, 66 are placed close to each other and are positioned approximately at the pupilary plane of a focusing lens 68 with a focal length f1, providing a focused spot in the resin mixture. Alternatively, one scanner is positioned at the focal position of lens 68, at a distance of f1 from the lens, and a relay lens 70 with focal length f2 is positioned at a distance of f1+f2 from the focussing lens 68. Consequently, the lenses 68, 70 establish a telescopic relay unit, with the second scanner unit 66 being positioned at a distance of f2 from the relay lens 70. If desired, an imaging lens 72 with focal length f3 can be positioned at a distance of f3 from the scanner 66, and the imaging lens 72 focuses the light energy into a spot in the resin mixture volume.

In addition to the exemplary scanning units described above, it is to be appreciated that any three-dimensional beam scanning device including the use of rotating polygon, or resonance scanning mirrors as beam steering elements can be used to direct and focus the irradiating energy.

Figure 5:
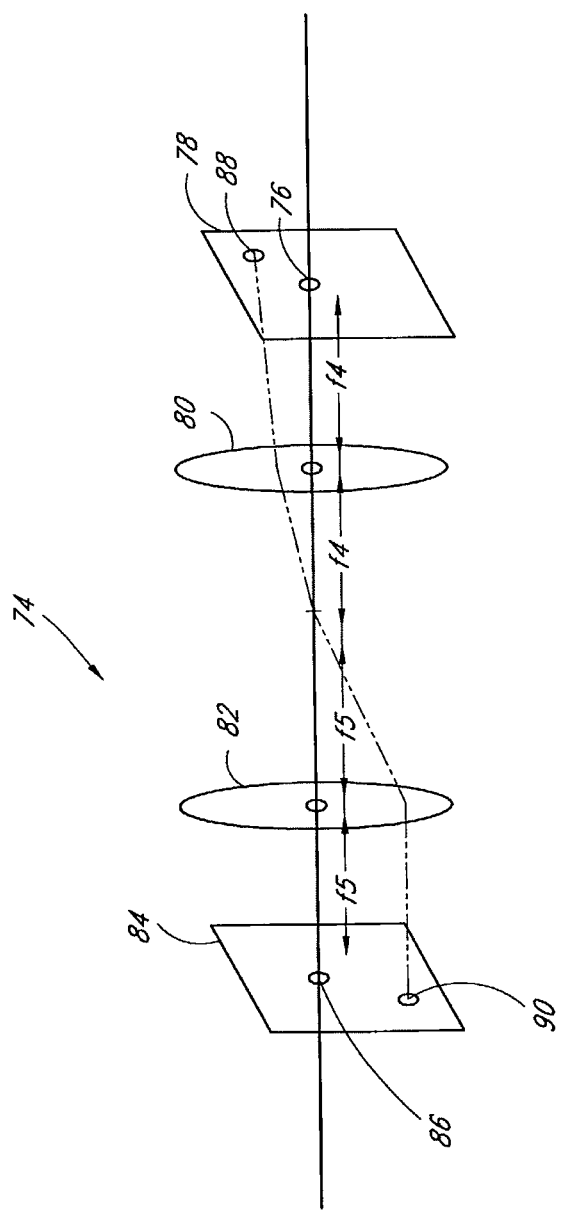
FIG. 5 is a schematic diagram of a fourth preferred apparatus for establishing a correcting element.

Indeed, another embodiment of a system for delivering curing light to specific locations in an resin mixture volume is shown in FIG. 5 and generally designated 74. The system 74 shown in FIG. 5 varies the location of the light source, shown at point 76, at the object plane, shown at 78. The system 74 includes, for the purpose of illustration, two lenses 80, 82 with focal lengths f4 and f5, respectively, that are respectively positioned a distance of f4 from the object plane 78 and f5 from an resin mixture object plane 84. Also, the lenses 80, 82 are separated from each other by a distance equal to the sum of their focal points (i.e., f4+f5). The radiation source indicated at 76 has a corresponding image point 86 at the resin mixture object plane 84. Likewise, for an off-axis light source location, e.g., as indicated at 88 on the object plane 78, there is a corresponding point location 90 on the resin mixture image plane 84. Accordingly, by moving the light source in the image plane 78 and by establishing an appropriate distance between the lenses 80, 82, the resin mixture of the present correcting element can be cured at various depths at various locations as appropriate to establish a wavefront correcting element.

Figure 6A:
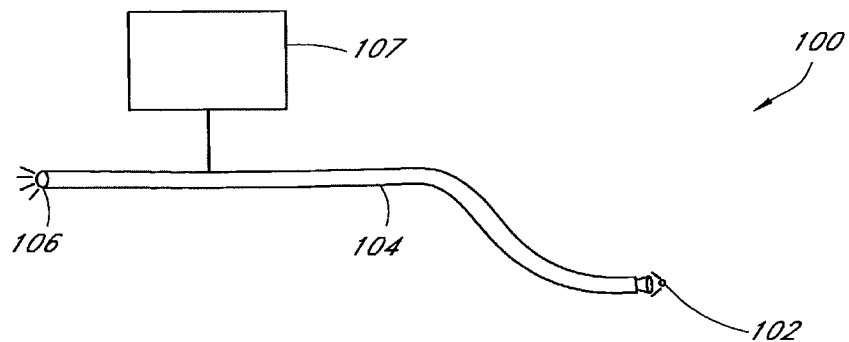
FIG. 6A is a schematic diagram of a fifth preferred apparatus for establishing a correcting element.

Still another system, generally designated 100, is shown in FIG. 6A. As shown, a single light source 102 is positioned adjacent an optical fiber 104, with the emitting, distal, end 106 of the fiber 104 being movable to various desired locations at the object plane of the resin mixture to be cured. The positioning of the optical fiber is controllable by mechanical positioning means 107 that can include motorized translation stages that are movable in three dimensional (XYZ) space to focus light at the target plane such that the radiation emitted from the fiber is delivered to a corresponding image location at the image plane. In this way, the photon energy is delivered through the imaging system to any desired location in the resin mixture volume.

Figure 6B:
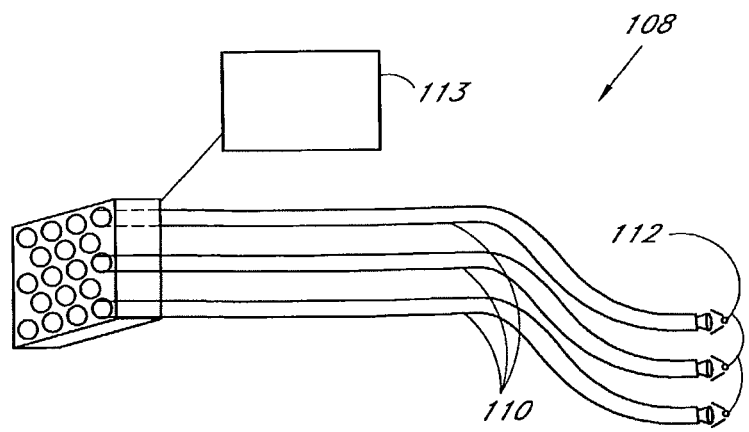
FIG. 6B is a schematic diagram of a sixth preferred apparatus for establishing a correcting element.

Alternatively, FIG. 6B shows a system 108 having a bundle of stationary fibers 110, each carrying light from a respective light source 112. The radiation intensity of each of source 112 is controllable by a computer. The fiber bundle configuration enables simultaneous multiple-point curing in the resin mixture, and therefore improves curing efficiency without compromising spatial resolution of the desired profile of the index of refraction change in the resin mixture. After the curing process is completed for each location of the fiber bundle, the fiber bundle is then moved to a different location by mechanical translation means 113 to create the index of refraction profile in the resin mixture.

Figure 7:
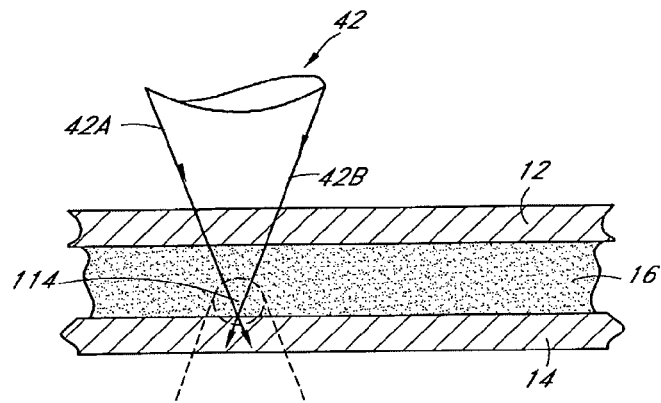
FIG. 7 is a cross-sectional view of corrective element shown in FIG. 1, taken along the line 7-7 in FIG. 1.
Figure 8:
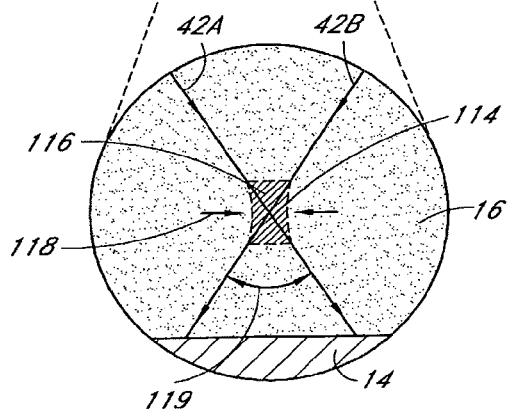
FIG. 8 is an enlarged view of a portion of FIG. 7.
Figure 9:
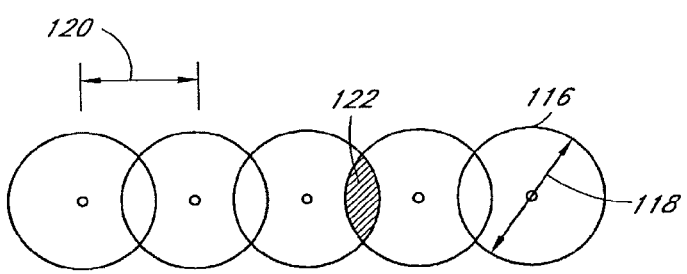
FIG. 9 is a schematic top view of a typical curing pattern within the resin mixture layer of the correcting element, showing the location and relationship between successive curing volumes within a layer of resin mixture.

Having set forth various apparatus for selectively irradiating the resin mixture 16 of the correcting element 10 shown in FIG. 1, reference is now made to FIGS. 7, 8, and 9, which show details of the resin mixture curing process. As shown in FIG. 7, the converging light beam 42 passes through the transparent plate 12 and converges within the resin mixture 16. Specifically, the light ray edges 42A and 42B of the beam 42 converge at a focal point 114 and define a curing volume 116 (FIG. 8) that has a so-called "beam waist" 118. The beam volume 116 represents the region in the resin mixture 16 which will be cured by exposure to the converging light beam 42. More specifically, the relatively tight focal point 114 of light beam 42 causes the spatially localized curing of the resin mixture 16 to form the curing volume 116. As set forth above, the light beam scanning apparatus is operated to move the focal point of the light beam to various points in the resin mixture to establish the desired curing pattern (light retardation) profile. Generally speaking, a beam 42 with a cone angle 119 that is in the range of 0.002 radians to 1.5 radians may be used.

FIG. 9 illustrates this. Because the preferred converging beam 42 in the present embodiment is conical in shape, the top view of each curing volume 116 is circular. Looking at FIG. 9 it can be appreciated that a series of light beams 42 may be used to form a continuous curing pattern through the resin mixture layer 16. In the event that a continuous curing pattern between successive curing volumes is desired, the distance 120 between curing volumes should be less than the diameter, i.e., the waist 118, of the curing volume 116, thereby establishing an overlap region 122 between adjacent curing volumes 116.

The size of the beam overlap region 122 can have a crucial effect on the overall homogeneity of the index of refraction of the cured resin mixture 16. In a preferred embodiment, the size of the beam overlap region 122 can vary between ten to seventy five percent (10%-75%) of the size of the beam waist 118 of the adjacent curing volumes. In a particularly preferred, non-limiting embodiment, the size of the beam overlap region 122 is between forty to sixty percent (40%-60%) of the size of the beam waist 118.

In one embodiment in which a tightly focused beam 42 configuration is preferred, the beam waist 118 is in the range of twenty microns (20 .mu.m) or less. However, beam waists between 0.1 microns and two hundred microns may be used. For the more demanding situations where the index profile is microscopic in dimensions, a diffraction limited focusing configuration with microscopic objective can be used. As an example, a light source can be used that produces a 350 nm wavelength light beam in conjunction with a beam focusing lens with a numerical aperture of 0.5. With this combination of structure, the beam waist 118 has a length of about 0.86 microns (0.86 .mu.m) in air, and in an resin mixture with an index of refraction of 1.54, as an example, the beam waist is 1.35 microns, with the depth of focus being 0.87 microns below the surface of the resin mixture.

It is to be understood that the curing volumes 116 within the resin mixture layer 16 can be sequential and contiguous to each other as shown in FIG. 9, or the scan sequence may be randomly accessed, such that the new curing location can be isolated from the previous location, with no overlap of the beam waists.

Figure 10:
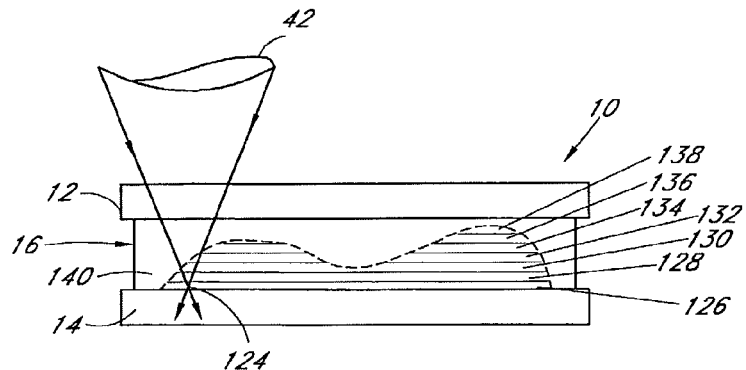
FIG. 10 is a schematic elevational view of the correcting element shown in FIG. 1, showing a three-dimensional curing pattern profile consisting of multiple layers of cured resin mixture, and schematically showing the light beams used to create the layers.

In contrast to FIG. 9, which shows a schematic plan view of a curing profile, FIG. 10 schematically illustrates an elevational view of the resin mixture to show an exemplary depth profile that can be achieved to establish a three-dimensional curing pattern profile. As stated above in reference to FIG. 2, the deeper regions of the resin mixture 16 preferably are cured first. This causes the formation of a curing volume 124. The focal point of the light beam is then moved as described above in the X-Y plane, thereby establishing a first cured layer 126 within resin mixture layer 16. Then, the depth of the focal point of the light beam is adjusted and the light beam moved in the X-Y plane to establish additional curing layers 128, 130, 132, 134, 136, 138.

Following the creation of a three-dimensional curing pattern profile shown in FIG. 10, excess, uncured resin mixture 140 may be removed from the correcting element 10 using a suitable solvent. Once removed, the volume previously occupied by the uncured resin mixture 140 may be refilled with an optically stable fluid which exhibits no refractive index change when exposed to radiation. Or, the volume may be refilled with same or similar resin mixture without any photo-initiator. Yet again, the volume can be refilled with resin mixture containing curing inhibitor such as phenol, or hydroquinone derivatives, which would inhibit any curing action even the resin mixture is exposed to radiation. As still another alternative, the volume can be refilled with another type of resin mixture having a desirable curing characteristic and with a predetermined index of refraction such that the final index of refraction profile in the wave plate is reached when all resin mixture in the confined volume is substantially cure, and such that exposure to sun light or other radiation shall not alter its refractive index profile. Still again, an optical coating can be applied on the plates 102, 104 to protect the resin mixture from exposure to a predetermined range of wavelengths that would otherwise cure the resin mixture.

By removing the uncured resin mixture and replacing its volume with or without an optically stable material, a stable correcting element 10 can be established that resists changes to its index of refraction under long term exposure to light sources. This is particularly useful in environments where the correcting element 10 would be exposed to sunlight or other light sources which might contain wavelengths which would cause further curing of the previously un-cured resin mixture 140.

Figure 11:
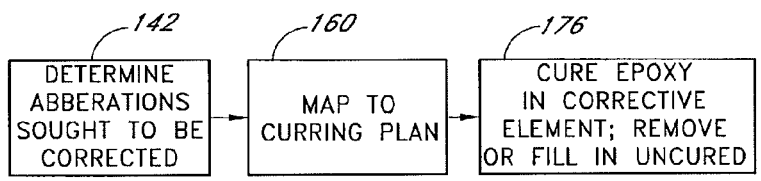
FIG. 11 is a flow chart of a process of forming a correcting element.

FIG. 11 shows the overall steps set forth above. Commencing at block 142, the aberrations, i.e., the wavefront, sought to be corrected is determined. To determine the wavefront, laser-based measuring techniques can be used. In one exemplary, non-limiting embodiment, wavefront sensing instruments such those manufactured by Visx, Santa Clara, Calif., or Zeiss/Humphrey Instruments, Dublin, Calif. can be used.

Figure 12:
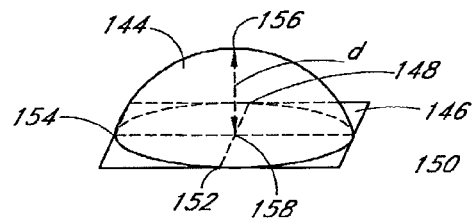
FIG. 12 is a schematic diagram of a wavefront.

Referring briefly to FIG. 12, a wavefront 144 is shown that for illustration is a divergent wave which may consist of spherical, astigmatism and high order aberrations. At an imaginary cross sectional plane 146, the wavefront has intersections located at points 148, 150, 152, 154. The peak of the wavefront is indicated at 156, which is traveling ahead of the intersections 148, 150, 152, 154. The distance between the peak 156 and the intersections is typical expressed in the units of physical distance in space. The peak 156 has a projected point 158 on the plane 146.

Figure 13:
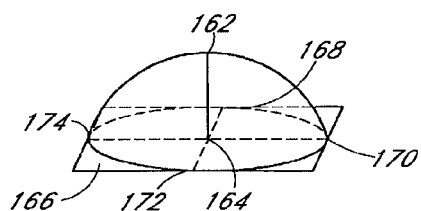
FIG. 13 is a schematic diagram of an index of refraction profile for curing a lens to compensate for aberrations shown in the wavefront of FIG. 12.

Accordingly, the logic of FIG. 11 moves from block 142 to block 160 to map the wave sought to be compensated to a resin mixture curing plan. The retardation profile can be determined, for example, by a computer which receives the determined wave front. The curing plan is used to create a curing profile that will vary the index of refraction of the resin mixture 16 to match the profile of the wave 144 such that a plane wave exits the correcting device 10. An illustrative curing profile is shown in FIG. 13, which has a three dimensional distribution profile 162 that is identical that of the profile of the wave 144 shown in FIG. 12.

Specifically, in one preferred, non-limiting embodiment, Software running on a computer would perform the following determination. Assume that the unit of retardation required for an ideal compensation can be calculated as follows. Further assume that the difference An of the index of refraction between cured and uncured resin mixture is known (typically in the range of 0.001 to 0.05). The maximum retardation required is the physical distance "d" between the wave 144 peak 156, and its projection point 158 on the plane 146. The required thickness of the resin mixture 16 consequently is at least d/.DELTA.n. In the curing profile for the resin mixture layer 16, the scale of the magnitude of the retardation is such that the magnitude of thickness of the cured resin mixture or the integrated index difference at a profile peak 162 to its projection 164 on a cross-sectional plane 166 is d/.DELTA.n. The effect of such a profile is that the peak 156 of the wave 144 will experience the most retardation, and the wave at the intersections 148, 150, 152, 154 experience no retardation at corresponding locations 168, 170, 172, 174 of the index profile which are in the uncured portion of the resin mixture 16. Accordingly, the resin mixture is cured such that it index of refraction establishes a profile that matches the profile of the wave sought to be compensated for.

Once the desired refraction profile is determined at block 160, the logic of FIG. 11 can move to block 176 to cure the resin mixture 16 in accordance with the curing plan. As mentioned above, uncured resin mixture can be removed from the correcting element 10.

In certain embodiments the resin mixture 16 need not necessarily be completely cured, depending on the curing plan. Partially cured resin mixture contributes less in the index of refraction change than a completely cured resin mixture for the same volume. Furthermore, a mixture of completely and partially cured resin mixture may also serve the purpose of wavefront compensation in one embodiment. It is the integrated retardation index of refraction profile, and not the actual physical shape of the cured resin mixture volume, that provides the necessary compensation and retardation of the wavefront.

The foregoing systems and methods can be useful in providing a stable optical wave plate which may exhibit any retardation level, with any spatial variation. Embodiments are applicable to correct distortion in a light beam of any desirable cross sectional area, and have the ability to correct not just low numbers of wave distortions in the range of a fraction of a wave to a few waves, but to correct up to hundreds of waves, covering and area ranging from less than a millimeter to several hundred millimeters. Embodiments are a stand-alone wavefront distortion corrector, and can include a refractive power correction.

Figure 14:
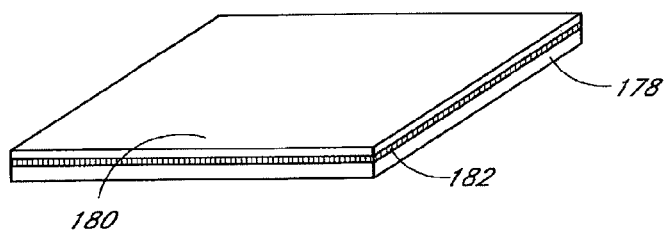
FIGS. 14, 15 and 16A-B show alternate configurations of the correcting element of the present invention.
Figure 15:
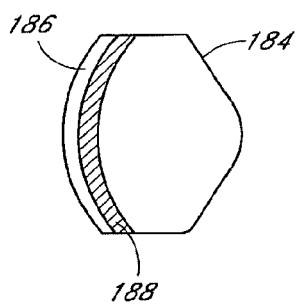

Indeed, turning to FIGS. 14-16, various other configurations of the correcting element can be seen. For example, as shown in FIG. 14, a mirror 178 has a surface non-flatness of more than one wavelength at 632 nm, generally considered to be of poor optical quality. To compensate, a transparent element 180, which is not necessarily of high surface quality, is used as a cover, and a layer of resin mixture 182 is filled between the transparent cover 180 and the mirror 178. The wavefront aberration of the combined elements is measured and mapped to a profile of a curing profile as described above to render a combined structure having a high optical quality with minimal aberrations. As an additional improvement, the outer surface of the mirror may be coated for UV blocking for stopping further curing and any change of the wavefront profile. Other methods of maintaining the index of refraction profile described earlier are also applicable.

FIG. 15 shows an embodiment of the correcting element configured as a lens 184. A transparent, nil-diffractive cover 186 can cover the lens 184 and can have either a convex or a concave shape that closely matches the surface of the lens 184. Neither the lens nor the cover plate need have a high surface quality tolerance. A layer of resin mixture 188 is disposed between the cover 186 and the lens 184 to compensate for imperfections in the lens 184 in accordance with principles set forth above.

Additionally, the embodiments of the present invention are particularly useful in the construction of improved ophthalmic lenses which have refractive power established in increments of fractions of a wavelength over the entire lens area, such that the lens produces localized wavefront correction tailored to the aberration of the eye of an individual. FIG. 16 shows such a correcting element.

Figure 16A:
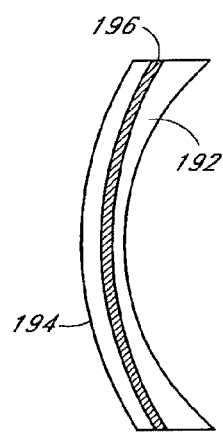
Figure 16B:
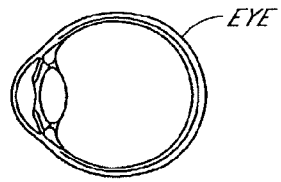

In a preferred embodiment, the aberrations of an eye are measured as described above. The outcomes of this wavefront measurement can include piston, tip, tilt, defocus (spherical power), astigmatism and its axis, and the higher order aberrations describable in Zernike polynomials. The prism (tip, tilt), spherical, and astigmatism components, which are referred to as refractive powers, can be corrected with currently available ophthalmic lens with the best possible match, typically limited to ⅛ diopter increments. The systems described above are then applied to complete the correction of aberrations including the residual of the sphere and astigmatism and the high order aberrations. In FIGS. 16A and 16B, a lens system includes a conventional ophthalmic lens 192, a cover lens 194, and a thin layer of resin mixture 196 disposed therebetween. As an example, the conventional lens 192 can be a lens with negative refractive power, typically for myopia patients, and the outer surface of the lens 192, i.e., the surface that is farthest away from the eye, has less curvature than the inner surface. The cover lens 194 may or may not have any focusing power, and it is preferably thin, to minimize the overall thickness of the combined lens system. It has a surface curvature closely matched with that of the outer surface of the conventional lens 192. The combined structure is then measured in accordance with present principles to determine the overall refractive power and aberration including the cover lens 194 and resin mixture 196. This is mapped to a curing plan for the resin mixture 196 by subtracting from the eye measurement the correction and aberration of the combined lens structure to render a residual aberration profile. Then the resin mixture 196 is cured to create an index of refraction profile according to the residual aberration profile to cancel the residual aberration. The area of the ophthalmic lens can be in the range of 3 mm to 70 mm, and not usually less than the pupil size of the patient. The optical center of the lens is then aligned with the entrance of the pupil location on a spectacle frame, and the lens is then cut to the correct size to fit into the spectacle for the patient.

Another application of embodiments of the present invention are improving the resolution of viewing instruments such as telescopes, microscopes, ophthalmic diagnostic instruments including confocal scanning ophthalmoscopes, and fundus cameras. In all cases, each viewing instrument includes refractive elements such lenses, reflective elements such as mirrors and beam splitters, and diffractive elements such as gratings and acousto- and electro-optical crystals. The present invention can eliminate costly manufacturing of such apparatus by using less costly optics and by compensating for the attendant residual aberrations with correcting elements such as are described above.

The aberrations of the selected optical system are first analyzed and measured and then mapped to a resin mixture curing plan for an appropriately configured correcting element, which cancels the wavefront aberrations of the optical system. The optical system being corrected can, if desired, include the aberrations introduced by a particular user's eye, so that these aberrations are also compensated for. In the case of a telescope, a correcting element of the present invention is positioned next to the objective lens of the telescope, where the image rays are approximately collimated. In the case of microscope, a correcting element is positioned next to the eyepiece.

In the case of fundus camera, which is compensated for similarly to microscope compensation, aberrations of the patient's eye to be examined may limit the resolution of the camera. If so, a correcting element of the present invention is first constructed to cancel the aberrations of the eye under cycloplegia conditions wherein the accommodative muscles of the eye are paralyzed, and a separate correcting element for the correction of the aberrations of the camera is constructed and is permanently attached to the camera.

Figure 17:
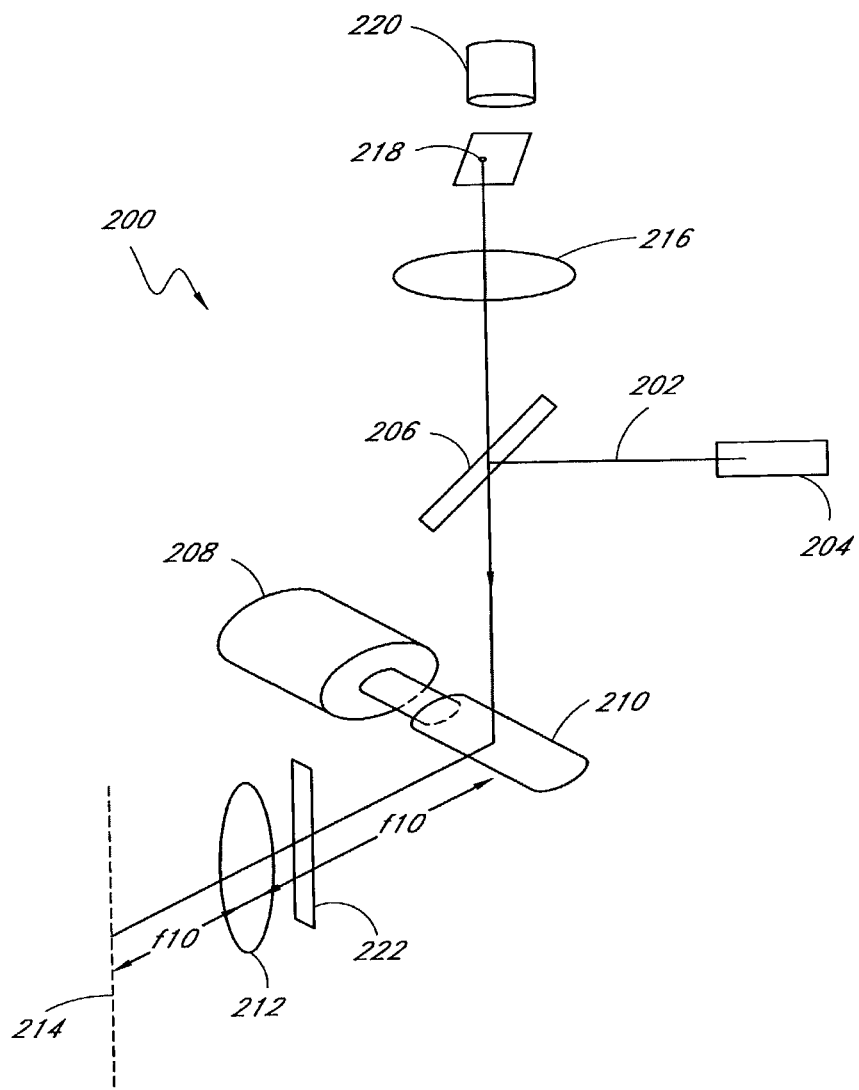
FIG. 17 is a schematic diagram showing one of the correcting elements in one intended environment to correct aberrations in an optical system.

FIG. 17 shows how a correcting element can be incorporated into a confocal scanning imaging system 200. A collimated light beam 202 from, e.g., a diode laser or a HeNe laser 204, is directed by a beam splitter 206 to a beam scanner unit 208. The beam splitter 206 can be a 50-50 beam splitter or a polarization beam splitter which has an appropriate coating to maximize the reflectivity for the incident and maximized transmission for the returned beam with the appropriate polarization characteristics. The scanner unit 208 has its scanner minor 210 positioned at the focal point of a focusing lens 212, which has a focal length of f10. The scattered light at a target point 214 is imaged through the lens 212, reflected by the scan mirror 210, and focused by a second lens 216 onto a pin hole 218. The light intensity is detected by a detector 220, and is recorded at each target position and processed for the reconstruction of a profile of the target. For two dimensional scanning, two additional relay lenses and a second scanner are inserted between the first scanner 208 and the focusing lens 212.

To attain improved performance of the system 200, a correcting element 222 in accordance with the foregoing teachings is positioned in the light path to correct the wavefront aberrations introduced by one or more of the above-mentioned components. Likewise, a correcting element can be positioned in the light path if desired.

Figure 18A:
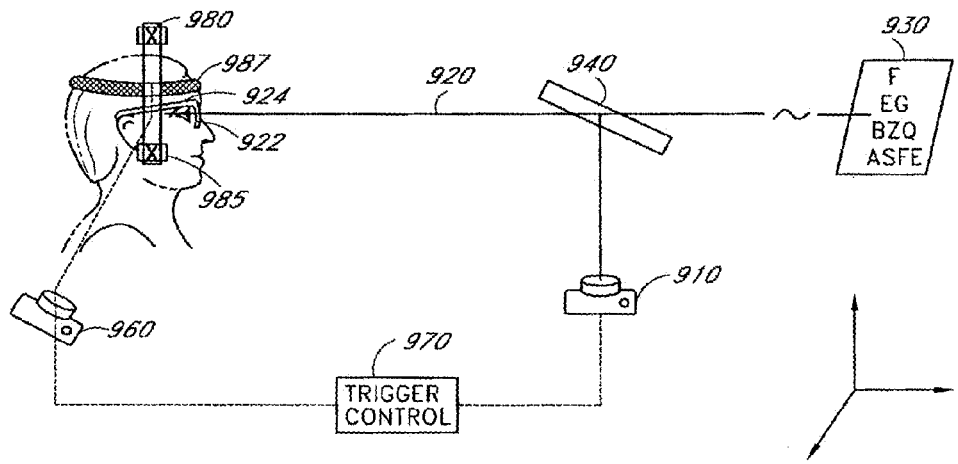
FIGS. 18A-B is a schematic diagram of an apparatus for measuring patient parameters.
Figure 18B:
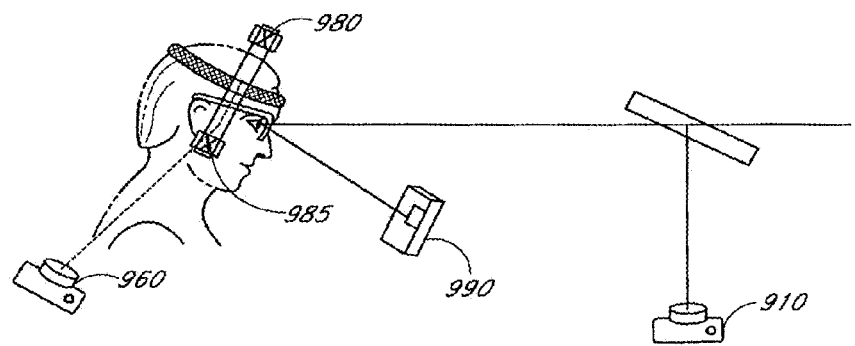

Now referring to FIGS. 18A and 18B, another application of an embodiment of the present invention is to provide customized progressive addition lenses (PAL) for presbyopic patients. Current progressive addition lenses have a fixed distance between the optical center for the distant vision and that of the near vision. Typically, the patient is fitted for the distant vision for a specific glasses frame of patient's choice. The patient must adapt to a specific viewing angle, by tilting of the head in order to find the best viewing angle for the near vision. This makes the experience of wearing the progressive addition lens unpleasant for a period of weeks or up to several months before the patient becomes accustomed to the lens.

With the above considerations in mind, a video image capture setup as shown in FIG. 18A can be used to capture the point of intercept of the patient's visual axis with a lens 922 in a trial frame 924 or in a frame selected by the patient. A video camera 910 is positioned at about 90 degrees from the line of sight 920 towards a standard test eye chart 930, and a beam splitter 940 is positioned in the line of sight and is oriented at about 45 degrees to direct an image en face to the patient's eye and the spectacle frame to the camera 910. The camera and the beam splitter can be positioned at any convenient location between the patient and the test eye chart. When the patient is examined in dim light conditions, additional near-infrared illumination at wavelengths longer than 700 nm may be applied to illuminate the eye for ensuring an adequate signal to the camera. The beam splitter may be coated for high transmission for the visible spectrum and for high reflectivity at the near infrared wavelength at 45 degrees. Depending on the location of choice of the camera, a zoom lens may be part of the focusing elements of the camera to bring in the image of the eye and the eyeglasses frame to sufficiently fill the image sensor of the camera.

The camera 910 first captures the location of the center of the pupil relative to the bottom of the eyeglasses frame when the patient is looking at a distant object (eye chart) 930. A second camera 960 positioned and pointed at the side of the patient head (90° en face) captures the tilt angle of the patient's head when the patient is reading a distant chart or object. The patient is instructed to view the distant object in a most comfortable and natural position. At that point, either the patient or the examiner pushes a switch in a trigger control 970 connected to the cameras 910 and 960 to record the relevant positions and angles in video images from the cameras 910 and 960.

For the near viewing measurements, the patient is then asked to read a book page, which is disposed at his natural reading position. Depending on the patient's need, the patient instead may be asked to view a display on a computer monitor. The camera 910 captures the change in the convergence of the eyeballs when patient is reading at a near distance. The camera 960 now captures the head tilt angle and the distance between the apex of the cornea to the spectacle lens, using a zoom feature of the camera, and the position of the reading material at the near viewing position without camera zooming. To more accurately pinpoint the patient's line of sight at the near viewing, the patient may be instructed to hold a printed page 990, as shown in FIG. 18B, and read a line at the center on the printed page, and the reading material can be sufficiently reduced in size to reduce variability. The tilt angle of the head can be deduced from the landmarks on the patient's head/ear, or two markers 980, 985 can be placed on the patient's head in near vertical alignment with a headband 987, for example.

Data analysis from the video images identify the tilt angle of the head at both distant viewing and near viewing, and the angle of the line of sight of the near viewing relative to that of distant viewing. The differences of the angles between the lines of sight and the respective tilt angles of the head correspond to the amount of eye rotation when the patient changes from distant to near viewing. From the apex distance of the spectacle lens, and the angle of the eyeball rotation, the actual distance between the distant optical center and the near optical center on the spectacle lens can be determined. This distance is unique and customized to the patient, since such a separation distance of the optical centers of the near and distant zones on the spectacle lens and their locations are customized for the natural reading and viewing habits of the patient, and the pupilary distances at the distant and near viewing.

The foregoing teachings are then applied to construct the added power of the progressive addition lens for the near viewing to the ophthalmic lens, using customized locations of the optical center for the distant viewing and the optical center for the near viewing for that patient. The design of the added power for a progressive addition lens is well known in the art. Alternatively lens design services can be obtained through lens providers such as Shamir Optical of Israel. The power profile of the progressive addition lens is then converted into the index of refraction change profile in the resin mixture layer. This eliminates the process which current progressive addition lens manufacturing requires, i.e., the making individual molds for each customized configuration.

While particular embodiments and examples are shown and described in detail herein it is to be understood they are representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

The invention claimed is:

1. An apparatus for curing at least one monomer in a resin mixture at a plurality of cure locations to thereby establish an index of refraction profile in the resin mixture, the resin mixture being positioned as a layer between a first optical element and a second optical element, the apparatus comprising:

at least one light source generating a light capable of curing the monomer in the resin mixture;

means for directing the light from the light source to the resin mixture and for focusing the light from the light source to converge to a focal point located within the layer of the resin mixture; and means for moving the focal point of the light in three dimensions from one cure location of the plurality of cure locations within the layer of the resin mixture to another cure location of the plurality of cure locations within the layer of the resin mixture.

2. The apparatus claim of 1, wherein the means for moving the focal point of the light is capable of moving the focal point so that the plurality of cure locations have no overlap.

3. The apparatus claim of 1, wherein the means for moving the focal point of the light is capable of moving the focal point so that neighboring sure locations of the plurality of cure locations overlap between 10 to 75% of a beam waist of the light.

4. The apparatus claim of 1, wherein the means for moving the focal point of the light is capable of moving the focal point so that neighboring cure locations of the plurality of cure locations overlap between 40 to 60% of a beam waist of the light.

5. The apparatus of claim 1, further comprising a determining means for determining a three dimensional spatial distribution comprising a compensation wavefront of the first optical element subtracted from a compensating wavefront of a patient's eye, wherein the three dimensional spatial distribution further comprises a residual compensating wavefront representing residual refractive power and high order aberrations of the patient's eye, the means for determining being operatively coupled to the means for moving the focal point so as to cure the at least one monomer in the resin mixture to form therein a three dimensional spatial distribution of the cured at least one monomer in the resin mixture.

6. The apparatus of claim 1, wherein the light source comprises at least one selected from an optical fiber or a fiber bundle that is coupled to a radiation source.

7. The apparatus of claim 1, wherein the means for moving the focal point of the light from one cure location to another cure location comprises at least one selected from the group consisting of a scanning unit and an X-Y-Z translation mechanism.

8. The apparatus of claim 1, wherein the first optical element comprises a component of an optical instrument.

9. The apparatus of claim 8, wherein the optical instrument is at least one selected from the group consisting of telescopes, microscopes, confocal scanning microscopes, and fundus cameras.

10. The apparatus of claim 1, wherein the first optical element comprises a customized ophthalmic lens for a patient.

11. The apparatus of claim 1, wherein the first optical element comprises a progressive ophthalmic lens customized to a patient's eye.

12. The apparatus of claim 11, wherein the customized ophthalmic lens comprises an optical center aligned with the center of an entrance pupil in a spectacle frame.

13. The apparatus of claim 11, wherein the customized ophthalmic lens is positioned in a spectacle frame.

14. The apparatus of claim 11, wherein the customized ophthalmic lens comprises an index of refraction profile that corrects aberrations of the customized ophthalmic lens.

15. The apparatus of claim 14, wherein the aberrations comprise refractive powers and higher order aberrations, wherein the refractive powers comprise spherical power, cylindrical power, and its orientation axis.

16. The apparatus of claim 1, wherein the index changing resin mixture is sandwiched between the first optical element and the second optical element.

17. The apparatus of claim 16, wherein at least one of the first optical element and the second optical element has a refractive power including a spherical and cylindrical power that closely matches corresponding components in high order aberrations of a patient's eye.

18. The apparatus of claim 1, wherein the means for moving the focal point of the light is capable of generating the plurality of cure locations within a diameter in the range of 3 mm-70 mm.

* * * * *